United States Patent
Toporov et al.

(10) Patent No.: US 6,415,009 B1
(45) Date of Patent: Jul. 2, 2002

(54) METHOD FOR PRODUCING A COILED BODY FOR IRRADIATING RADIOACTIVE RADIATION

(75) Inventors: Youri Genadievich Toporov; Vyacheslav Terentyevich Filimonov, both of Dimitrovgrad (RU); Vladimir S Shokurov, Kharkov (UA)

(73) Assignee: Acrostak Co. (CH)

( * ) Notice: Subject to any disclaimer, the term of this patent is extended or adjusted under 35 U.S.C. 154(b) by 0 days.

(21) Appl. No.: 09/351,842

(22) Filed: Jul. 13, 1999

(30) Foreign Application Priority Data

Oct. 30, 1998 (EP) .............................. 98120702

(51) Int. Cl.⁷ ................................. G21G 1/06
(52) U.S. Cl. .................. 376/158; 600/1; 600/3
(58) Field of Search .................. 600/1–8; 606/192; 376/158

(56) References Cited

U.S. PATENT DOCUMENTS

| 4,819,618 | A | * | 4/1989 | Liprie |
| 5,059,166 | A | * | 10/1991 | Fischell et al. |
| 5,728,042 | A | * | 3/1998 | Schwager |
| 5,924,974 | A | * | 7/1999 | Loffler |
| 6,024,690 | A | * | 2/2000 | Lee et al. |
| 6,030,333 | A | * | 2/2000 | Sioshansi et al. |
| 6,056,686 | A | * | 5/2000 | Mawad |
| 6,146,322 | A | * | 11/2000 | Papirov et al. |
| 6,149,574 | A | * | 11/2000 | Trauthen et al. |
| 6,196,996 | B1 | * | 3/2001 | Teirstein |
| 6,203,485 | B1 | * | 3/2001 | Urick |

FOREIGN PATENT DOCUMENTS

| EP | 0 633 041 | | 11/1995 |
| EP | 0 686 342 | | 12/1995 |
| EP | 778051 | * | 6/1997 |
| EP | 0 778 051 | | 11/1997 |
| WO | WO 93/04735 | | 3/1993 |

* cited by examiner

*Primary Examiner*—Charles T. Jordan
*Assistant Examiner*—Troy Chambers
(74) *Attorney, Agent, or Firm*—Anthony J. Casella; Gerald E. Hespos

(57) ABSTRACT

The method comprises the steps of forming an elongated tubular metal casing 1. This elongated tubular metal casing 1 is then coiled. The coiled tubular casing 11 is filled with a material 9 capable to irradiate radioactive radiation. The material 9 is in liquid state with following crystallization in the coiled tubular casing 11. The filled coiled tubular casing 11 is then sealed at its ends 5.

31 Claims, 1 Drawing Sheet

METHOD FOR PRODUCING A COILED BODY FOR IRRADIATING RADIOACTIVE RADIATION

BACKGROUND OF THE INVENTION

Invention relates to a method for producing a coiled body for irradiating radioactive radiation.

Coiled bodies for irradiating radioactive radiation are of particular interest in brachytherapy, and more particularly in endoluminal brachytherapy and percutaneous transluminal brachytherapy to promote an appropriate elasticity for handling the source through narrow and tortuous locations such as blood vessels.

For example, U.S. Pat. No. 5,059,166 describes an intra-arterial stent intended to inhibit intimal hyperplasia by means of radioactive radiation. The document refers to a radioisotope integral to an arterial stent which can irradiate the tissue in proximity to the implantation of the stent. In one embodiment, a helical coil spring stent is fabricated from a pure metal or alloy which has been activated so that it has become a radioisotope. In another configuration, the stent spring wire is made from a metal such as steel into which is alloyed an element that can be made into a radioisotope. In a further configuration, the stent wire is made from a radioisotope core material with an outer covering that has the attributes for being a coil spring. In a variant, the stent wire is made of a radioisotope coating plated onto a spring material core. Still in a further embodiment, a core of some material suitable for stents is plated with a radioisotope coating which is in turn coated with an anti-thrombogenic coating such as carbon.

The document EP-0633041-A1 outlines the use of a radioactive emitter in the form of a filament of small diameter which may be a coiled filament. Filament technology has the advantage of a dens concentration of the radioactive dose in a small volume of the source allowing a reduced diameter and a better manoeuvrability in narrow and tortuous vessels.

The document EP-0686342-A1 shows a further step in filament technology by having a filament, which may be in the form of a coil, coated by a neutral material such as Titanium.

The document EP-0778051-A1 shows a filament for irradiating a living body, comprising a core of material capable of irradiating radioactive radiation after activation, such core being clad in a casing of protective material. To achieve this structure, there is provided a method comprising the steps of forming an initial billet of core material capable to irradiate radioactive radiation after activation, forming an initial tubular preform of casing material, working both said initial billet and tubular preform until they have a grain size equal to or less than 30 $\mu$m, inserting the billet into the tubular preform to form an assembly, drawing the assembly through a series of successive dies of decreasing size with intermediate annealing of the assembly in intervals between successive dies until the assembly has a final outer diameter, and end sealing the casing material on the core material. The drawn assembly may be coiled before end sealing of the casing material on the core material. The core material may be Yttrium or Thulium with a casing material of Titanium.

The document WO 93/04735 shows various embodiments of an apparatus for the treatment of an artery, comprising a radioactive dose and means operatively connected to the dose for bringing it into a selected region of the artery. In one embodiment, the apparatus is comprised of a wire wound sheath removably positioned over a windowed housing formed of a wire winding containing a radioactive dose, whereby relative motion between the sheath and the housing permits moving the windowed housing in and out of the sheath to expose the radioactive dose in the artery.

SUMMARY OF THE INVENTION

It is an object of this invention to improve the possibilities of manufacturing coiled sources intended to irradiate radioactive radiation. It is a further object of the invention to propose a method for producing a coiled body for irradiating radioactive radiation which is highly versatile and which substantially enlarges the possibilities of using radioactive treatment.

To this effect, there is provided a method for producing a coiled body for irradiating radioactive radiation, comprising the steps of forming an elongated tubular metal casing, coiling said elongated metal casing, filling said coiled tubular casing with a material capable to irradiate radioactive radiation, and end sealing said coiled tubular casing. Accordingly, a very large choice becomes possible in terms of half-life period and energy of the materials capable to irradiate radioactive radiation rather than in terms of their capability to match with a protective coating. The intrinsic quality of the coiled tubular casing is not affected by problems of joint deformation with the material capable to irradiate radioactive radiation. The risks of cracks or rupture of the coiled body are practically eliminated, and efficiency of the coiled body raises. As the choice for the materials capable to irradiate radioactive radiation is far broader, such a choice may be oriented towards materials having higher irradiating energy and longer half-life periods. This may have a positive effect for the patients as radiation duration may be reduced with consequent reduction of pain, stress, and interruption of the blood flow in case of irradiation inside a blood vessel. Logistics may also be simplified because of the possibility of treating more patients with the same source. There are less transports and handlings of radioactive materials.

Preferably, the elongated tubular metal casing is formed by drawing or by grinding an initial tubular preform, or still by drawing an initial tubular preform and subsequent grinding thereof to assure inherent reliability of the casing tightness.

Preferably, the tubular metal casing will be formed to an outer diameter comprised between 100 and 150 $\mu$m and/or to an inner diameter comprised between 30 and 100 $\mu$m to secure miniaturization reducing trauma potential to the treated organs and radiation absorption by the casing wall.

Advantageously, coiling the elongated tubular metal casing comprises the steps of filling the elongated tubular metal casing with a liquid, end sealing the liquid filled elongated tubular metal casing, coiling the liquid filled elongated tubular metal casing on a mandrel, unsealing the liquid filled coiled tubular casing, and removing the liquid from the coiled tubular casing. Coiling the elongated tubular metal casing in such a way raises flexibility of the casing and secures the internal lumen of the casing against collapse during the coiling procedure. Uniform filling of the coiled tubular casing with the material capable to irradiate radioactive radiation is thus secured.

Preferably, filling of the coiled tubular casing is made with the material capable to irradiate radioactive radiation in liquid state with its following crystallization in the coiled tubular casing to promote uniform distribution of the said material inside the coiled casing and consequently uniform distribution of the radioactive activity throughout the coiled casing.

Advantageously, such a crystallization may be achieved by cooling. Furthermore, crystallization may be followed by radiation chemical decomposition to transform the material into non-melting and hard-leaching form to exclude material transformation into liquid phase and possible flowing thereof out of the coiled casing.

Preferably, nitrate crystallohydrate compounds of said material capable to irradiate radioactive radiation are used as said material in liquid state.

Preferably, carboxylic acid salts taken with said material in liquid state in mole relation 4:1 are used as said material in liquid state. And palmitic acid is advantageously used as said carboxylic acid salts.

Advantageously, phosphorous-organic acid salts taken with said material in proportion 4:1 are used as said material capable to irradiate radioactive radiation in liquid state. Preferably, diphenilphosphinic acid is used as said phosphorous-organic acid.

Advantageously, mixed salts of highest carboxylic and acetic acids are used as said material capable to irradiate radioactive radiation in liquid state.

According to a further aspect of the invention, filling of the coiled tubular casing is made with a gas state decomposition of said material capable to irradiate radioactive radiation and settling of said decomposition in the coiled tubular casing to also promote uniform distribution of the said material inside the coiled casing and uniform distribution of the radioactive activity throughout the coiled casing.

Still a further aspect of the invention provides for filling of the coiled tubular casing with said material capable to irradiate radioactive radiation in solid state. Preferably, such filling is made with the material in the form of a powder for a high degree of uniformity of the material distribution inside the coiled tubular casing. Alternatively, filling of the coiled tubular casing may be made with the material in the form of a wire or with the material coated on a wire.

Preferably, filling of the coiled tubular casing with the material in solid state is made by covering on the fire.

Preferably, the material in solid state is tightened after filling to raise the strength of the material.

Advantageously, tightening is made by an explosion in liquid, or by isotonic pressing, or still by magnetoimpulsive treatment.

Preferably, end sealing of the coiled tubular casing is made by laser bonding, or electronic beam welding, or optical welding, or electric arc welding, or still by soldering. Alternatively, it is advantageous to make end sealing of the coiled tubular casing by covering its ends and subsequent melting or annealing. It was also ascertained that sealing of the coiled tubular casing was appropriately made by mechanical plugging of elements having shape memory.

Preferably, the material capable to irradiate radioactive radiation is selected from the group of Cerium 144, Strontium 89, Strontium 90, Yttrium 91, Ruthenium 106, or Iodine 125, in active state.

Alternatively, the material capable to irradiate radioactive radiation is selected from the group of Tungsten 186, Iridium 191, Gadolinium 152, or Ytterbium 168, in non-active state. In such a case, the material in non-active state is activated after the step of end sealing the coiled tubular casing. And activation will be advantageously achieved by neutrons in a nuclear reactor.

In all its forms, the method according to the invention may include the step of cutting the filled coiled tubular casing into a plurality of coils before the step of end sealing the filled coiled tubular casing, whereby end sealing will be made on each of the cut coils.

These and other objects, features and details of the invention will become readily apparent from the following description with reference to the accompanying drawings which illustrate, diagrammatically and by way of example only, steps of the method according to the invention.

DETAILED DESCRIPTION OF THE INVENTION

Figure 1:
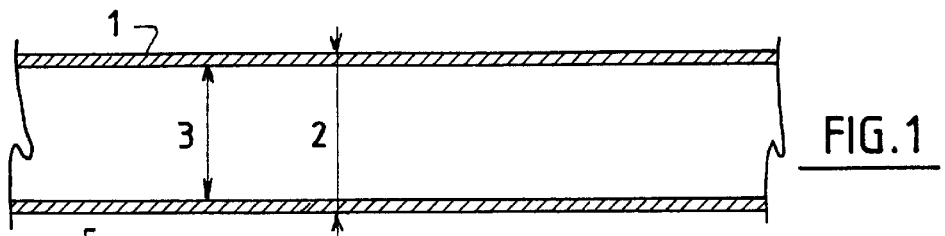
FIG. 1 shows an elongated tubular casing.

The method for producing a coiled body for irradiating radioactive radiation, starts from the step of forming an elongated tubular metal casing 1 as shown in FIG. 1. For example, this elongated tubular metal casing 1 may be formed by drawing an initial tubular preform (not shown), or by grinding said initial tubular preform, or by drawing said initial tubular preform and then grinding it. Preferably the elongated tubular metal casing 1 will have an outer diameter 2 comprised between 100 and 150 $\mu$m, and an inner diameter 3 comprised between 30 and 100 $\mu$m.

Figure 2:
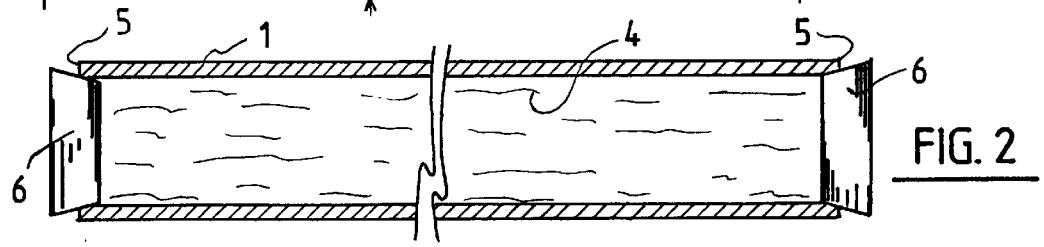
FIGS. 2 to 4 show the coiling of the elongated tubular casing of FIG. 1.
Figure 3:
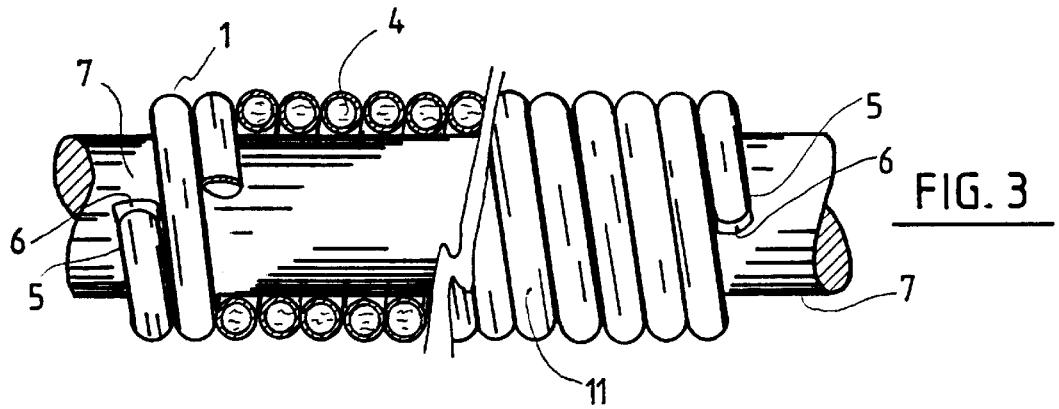
Figure 4:
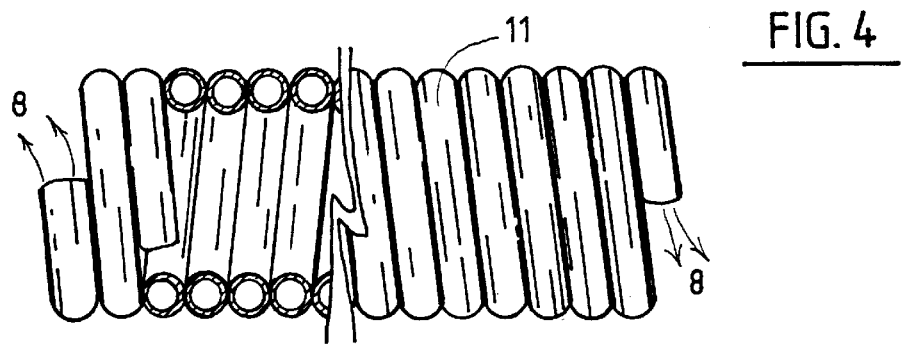

The elongated tubular metal casing 1 is then coiled and to achieve such a coiling, said elongated tubular casing 1 is advantageously filled with a liquid 4 (FIG. 2) and sealed at its ends 5, for example by means of plugs 6. The liquid filled casing 1 is then coiled on a mandrel 7, as shown in FIG. 3, and then, the plugs 6 are withdrawn and the liquid 4 is removed from the coiled tubular casing 11 as shown by arrows 8 on FIG. 4.

Figure 5:
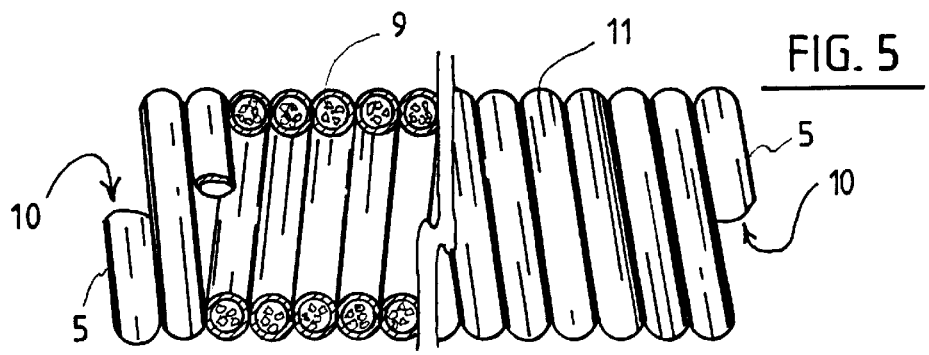
FIG. 5 illustrates the filling of the coiled tubular casing of FIGS. 4.

The coiled tubular casing 11 is then filled with a material 9 capable to irradiate radioactive radiation, as shown by arrows 10 on FIG. 5.

The material 9 is in liquid state with its following crystallization in the coiled tubular casing. Crystallization may be achieved by cooling and it may be followed by radiation chemical decomposition.

Nitrate crystallohydrate compounds of the material 9 may be used as the material in liquid state. Alternatively, carboxylic acid salts taken with material 9 in mole relation 4:1 may be used as material in liquid state, and palmitic acid may be used as said carboxylic acid salts. Still alternatively, phosphorous-organic acid salts taken with the said material in proportion 4:1 may be used as the said material, with diphenilphosphinic acid being used as said phosphorous-organic acid. Still as a further alternative, mixed salts of highest carboxylic and acetic acids may be used as the said material in liquid state.

Then, the coiled tubular casing 11 is sealed at its ends 5, for example by mechanical plugging of elements (not shown) having shape memory. Alternatively, sealing of the coiled tubular casing 11 may be made by laser bonding, or by electronic beam welding, or by optical welding, or by electric arc welding, or by soldering, or by covering the ends 5 and subsequent melting, or still by covering the ends 5 and subsequent annealing.

As a variant, the coiled tubular casing 11 may be filled with a gas state decomposition of the material capable to irradiate radioactive radiation and settling of said decomposition in the coiled tubular casing 11.

As a further variant, the coiled tubular casing 11 may be filled with the material capable to irradiate radioactive radiation in solid state or in the form of a powder, or in the form of a wire, or coated on a wire. The material may be tightened after filling, for example by an explosion in liquid, or by isotonic pressing, or still by magnetoimpulsive treatment. Where the material is in solid state, filling may be made by covering on the fire.

As the material capable to irradiate radioactive radiation, a selection is made from the group of Cerium 144, Strontium 89, Strontium 90, Yttrium 91, Ruthenium 106 or Iodine 125, in active state.

Alternatively, the selection may be made from the group of Tungsten 186, Iridium 191, Gadolinium 152, or Ytterbium 168, in non-active state, the material being activated after the step of end sealing of the coiled tubular casing 11. Activation may be made by neutrons in a nuclear reactor.

The filled coiled tubular casing 11 may be cut into a plurality of coils before sealing of the ends 5, end sealing being then made on each of the cut coils.

What is claimed is:

1. A method for producing a coiled body for irradiating radioactive radiation, comprising the steps:
    forming an elongated tubular metal casing (1);
    filling said elongated tubular metal casing (1) with a liquid (4);
    end sealing (5,6) said liquid filled elongated tubular metal casing (1);
    coiling said liquid filled elongated tubular metal casing (1) on a mandrel (7);
    unsealing said liquid filled coiled tubular casing (11);
    removing said liquid (4) from said tubular casing (11);
    filling said coiled tubular casing (11) with a material capable to irradiate radioactive radiation; and,
    end (5) sealing said coiled tubular casing (11).

2. A method according to claim 1, wherein said elongated tubular metal casing (1) is formed by drawing an initial tubular preform.

3. A method according to claim 1, wherein said elongated tubular metal casing (1) is formed by grinding an initial tubular preform.

4. A method according to claim 1, wherein said elongated tubular metal casing (1) is formed by drawing an initial tubular preform and subsequently grinding said drawn preform.

5. A method according to claim 1, wherein said elongated tubular metal casing (1) is formed to an outer diameter comprised between 100 and 150 $\mu$m.

6. A method according to claim 1, wherein said elongated tubular metal casing (1) is formed to an inner diameter comprised between 30 and 100 $\mu$m.

7. A method according to claim 1, wherein end (5) sealing of said coiled tubular casing (11) is made by laser bonding.

8. A method according to claim 1, wherein end (5) sealing of said coiled tubular casing (11) is made by electronic beam welding.

9. A method according to claim 1, wherein end (5) sealing of said coiled tubular casing (11) is made by optical welding.

10. A method according to claim 1, wherein said material is selected from the group of Cerium 144, Strontium 89, Strontium 90, Yttrium 91, Ruthenium 106, and Iodine 125, in active state.

11. A method according to claim 1, wherein said material is selected from the group of Tungsten 186, Iridium 191, Gadolinium 152, Ytterbium 168, in non-active state.

12. A method according to claim 11, wherein said material in non-active state is activated after the step of end sealing the coiled tubular casing (11).

13. A method according to claim 12, wherein activation is made by neutrons in a nuclear reactor.

14. A method according to claim 1, further comprising the step of cutting the filled coiled tubular casing (11) into a plurality of coils before the step of end sealing said coiled tubular casing, whereby end sealing is made on each of said cut coils.

15. A method for producing a coiled body for irradiating radioactive radiation, comprising the steps:
    forming an elongated tubular metal casing (1);
    coiling said elongated tubular metal casing (1);
    filling said coiled tubular casing (11) with a material capable to irradiate radioactive radiation, wherein the filling of said coiled tubular casing (11) is made with said material in liquid state (9) with its following crystallization in the coiled tubular casing (11); and,
    end (5) sealing said coiled tubular casing (11).

16. A method according to claim 15, wherein nitrate crystallohydrate compounds of said material are used as said material in liquid state (9).

17. A method according to claim 15, wherein carboxylic acid salts taken with said material in liquid state in mole relation 4:1 are used as the said material in liquid state (9).

18. A method according to claim 17, wherein palmitic acid is used as said carboxylic acid salts.

19. A method according to claim 15, wherein phosphorous-organic acid salts taken with said material in liquid state (9) in proportion 4:1 are used as the said material in liquid state (9).

20. A method according to claim 19, wherein diphenilphosphinic acid is used as said phosphorous-organic acid.

21. A method according to claim 15, wherein mixed salts of highest carboxylic and acetic acids are used as said material in liquid state (9).

22. A method according to claim 15, wherein said crystallization is achieved by cooling.

23. A method according to claim 15, wherein said crystallization is followed by by radiation chemical decomposition.

24. A method for producing a coiled body for irradiating radioactive radiation, comprising the steps:
    forming an elongated tubular metal casing (1);
    coiling said elongated tubular metal casing (1);
    filling said coiled tubular casing (11) with a material capable to irradiate radioactive radiation, wherein filling of said coiled tubular casing (11) is made with a gas state decomposition of said material and settling of said decomposition in said coiled tubular casing; and,
    end (5) sealing said coiled tubular casing (11).

25. A method for producing a coiled body for irradiating radioactive radiation, comprising the steps:
    forming an elongated tubular metal casing (1);
    coiling said elongated tubular metal casing (1);
    filling said coiled tubular casing (11) with a material capable to irradiate radioactive radiation, wherein filling of said coiled tubular casing (11) is made with said material in the form of a powder; and,
    end (5) sealing said coiled tubular casing (11).

26. A method for producing a coiled body for irradiating radioactive radiation, comprising the steps:
    forming an elongated tubular metal casing (1);
    coiling said elongated tubular metal casing (1);

filling said coiled tubular casing (11) with a material capable to irradiate radioactive radiation, wherein said filling of said coiled tubular casing (11) is made with said material coated on a wire; and, end (5) sealing said coiled tubular casing (11).

27. A method for producing a coiled body for irradiating radioactive radiation, comprising the steps:

forming an elongated tubular metal casing (1);

coiling said elongated tubular metal casing (1);

filling said coiled tubular casing (11) with a material capable to irradiate radioactive radiation; and, end (5) sealing said coiled tubular casing (11), wherein the end (5) sealing of said coiled tubular casing (11) is made by electric arc welding.

28. A method for producing a coiled body for irradiating radioactive radiation, comprising the steps:

forming an elongated tubular metal casing (1);

coiling said elongated tubular metal casing (1);

filling said coiled tubular casing (11) with a material capable to irradiate radioactive radiation; and, end (5) sealing said coiled tubular casing (11), wherein the end (5) sealing of said coiled tubular casing (11) is made by soldering.

29. A method for producing a coiled body for irradiating radioactive radiation, comprising the steps:

forming an elongated tubular metal casing (1);

coiling said elongated tubular metal casing (1);

filling said coiled tubular casing (11) with a material capable to irradiate radioactive radiation; and, end (5) sealing said coiled tubular casing (11), wherein the end (5) sealing of said coiled tubular casing (11) is made by covering said ends and subsequent melting.

30. A method for producing a coiled body for irradiating radioactive radiation, comprising the steps:

forming an elongated tubular metal casing (1);

coiling said elongated tubular metal casing (1);

filling said coiled tubular casing (11) with a material capable to irradiate radioactive radiation; and, end (5) sealing said coiled tubular casing (11), wherein the end (5) sealing of said coiled tubular casing (11) is made by covering said ends and subsequent annealing.

31. A method for producing a coiled body for irradiating radioactive radiation, comprising the steps:

forming an elongated tubular metal casing (1);

coiling said elongated tubular metal casing (1);

filling said coiled tubular casing (11) with a material capable to irradiate radioactive radiation; and, end (5) sealing said coiled tubular casing (11), wherein the end (5) sealing of said coiled tubular casing (11) is made by mechanical plugging of elements having shape memory.

* * * * *